(12) United States Patent
Webb et al.

(10) Patent No.: US 8,695,469 B2
(45) Date of Patent: Apr. 15, 2014

(54) COTTON DISPENSER

(76) Inventors: Trecia Ann Webb, Crown Point, IN (US); Jacob David Webb, Crown Point, IN (US)

( * ) Notice: Subject to any disclaimer, the term of this patent is extended or adjusted under 35 U.S.C. 154(b) by 491 days.

(21) Appl. No.: 12/971,837

(22) Filed: Dec. 17, 2010

(65) Prior Publication Data

US 2012/0152076 A1 Jun. 21, 2012

(51) Int. Cl.
*B26D 5/20* (2006.01)
*B65H 35/00* (2006.01)

(52) U.S. Cl.
USPC ............... 83/649; 83/225; 83/241; 83/436.1; 83/949

(58) Field of Classification Search
USPC ............... 83/203, 649, 650, 225, 436.1, 949, 83/241–243; 225/11, 46, 91, 39, 67, 61; 132/322, 325; 221/30–32, 197; 242/588.6, 590, 588, 570, 911, 526, 242/527, 527.1, 523–523.1, 588.3, 564.4; 206/409, 233
See application file for complete search history.

(56) References Cited

U.S. PATENT DOCUMENTS

| | | | | |
|---|---|---|---|---|
| 1,518,749 | A * | 12/1924 | Nelson | 225/67 |
| 2,645,543 | A * | 7/1953 | Mancini | 83/614 |
| 3,152,739 | A * | 10/1964 | McWilliams | 225/46 |
| 3,177,750 | A * | 4/1965 | Amemiya | 83/241 |
| 3,231,164 | A | 1/1966 | Seidler | |
| 3,392,895 | A * | 7/1968 | Ellner et al. | 226/138 |
| 3,494,235 | A * | 2/1970 | Postolowski | 83/225 |
| 4,569,467 | A * | 2/1986 | Kaminstein | 242/563 |
| 4,738,176 | A * | 4/1988 | Cassia | 83/208 |
| 5,027,974 | A * | 7/1991 | Porter et al. | 221/196 |
| 5,107,734 | A * | 4/1992 | Armbruster | 83/205 |
| 5,358,370 | A * | 10/1994 | Carpentier | 414/24.6 |
| 5,645,206 | A * | 7/1997 | Ippisch | 225/10 |
| 5,713,678 | A * | 2/1998 | Smith et al. | 400/613 |
| 5,860,561 | A | 1/1999 | Saldana et al. | |
| RE36,143 | E * | 3/1999 | Kind et al. | 83/13 |
| 6,749,148 | B2 * | 6/2004 | Helfer-Grand | 242/564.1 |
| 7,069,972 | B1 * | 7/2006 | Edelstein | 156/767 |
| 7,762,492 | B2 * | 7/2010 | Muderlak et al. | 242/525 |
| 7,963,201 | B2 * | 6/2011 | Willoughby et al. | 83/210 |
| 8,196,774 | B1 * | 6/2012 | Clarke et al. | 221/197 |

* cited by examiner

*Primary Examiner* — Laura M Lee
(74) *Attorney, Agent, or Firm* — Dale J. Ream

(57) ABSTRACT

A cotton dispenser includes a spool configured to receive a cotton strand thereabout and that rotates when the cotton strand is unwound therefrom. The dispenser includes a feed assembly downstream from the spool configured to receive an end of the cotton strand and unwind it from the spool when actuated. A cutting assembly is downstream from the feed assembly and configured to receive the cotton strand from the feed assembly. The cutting assembly includes a blade movable from a retracted configuration not in contact with the cotton strand and an activated configuration that severs the received cotton strand. The cotton dispenser includes a discharge chute in operative communication with the cutting assembly for guiding severed cotton portions to an outlet opening. A first input switch is electrically configured to actuate the feeding assembly so long as the input button is depressed and to actuate the cutting assembly when released.

8 Claims, 6 Drawing Sheets

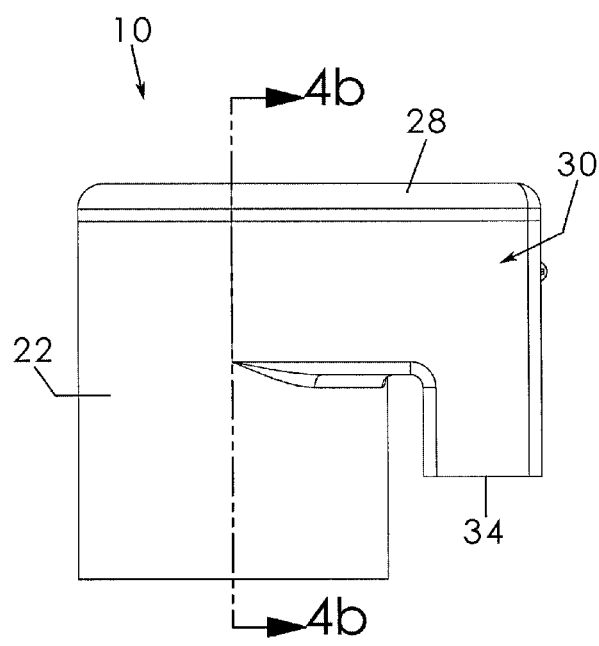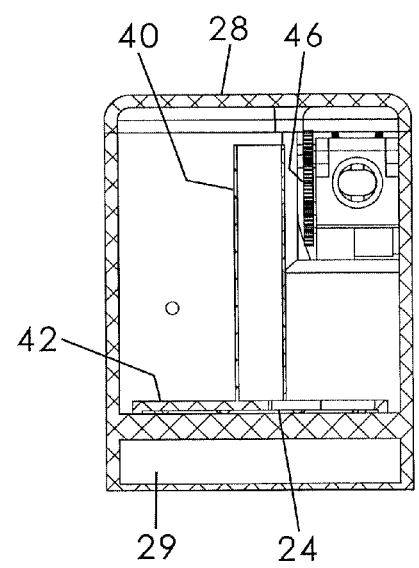
Fig. 4a
Fig. 4b

COTTON DISPENSER

BACKGROUND OF THE INVENTION

This invention relates generally to dispensing devices and, more particularly, to a dispenser of cotton material in user-defined portions. With the present invention, a user is able to obtain cotton ball type material of selected sizes automatically upon the press of a button.

Cotton balls or swabs are most often used in the medical community during medical procedures, whether to apply a medicament such as iodine to a wound, to absorb fluids such as blood, or to wipe away unsanitary substances. Similarly, cotton balls are often used in the home environment for similar purposes. Cotton materials used for these purposes are often sold in packages of multiple predetermined size balls or in bulk form in which individual pieces must be torn off for use.

Although assumably effective for their intended use, both types of traditional packaging has its disadvantages. For instance, to obtain a single cotton ball from a package of cotton balls requires a user to physically handle multiple balls that may be stuck together and then return unneeded cotton balls to the package. Similarly with a bulk of cotton material, the entire bulk must be physically handled in order to tear off a desired quantity. In either case, the required handling of the cotton may introduce undesirable contamination to unused cotton balls or to the bulk of cotton.

Therefore, it would be desirable to have a cotton dispenser that is powered and which dispenses the precise amount of cotton desired by a user. Further, it would be desirable to have a cotton dispenser that does not require any physical handling of stored cotton by a person. In addition, it would be desirable to have a cotton dispenser that enables a user to pre-load or re-load a spool of cotton into a housing.

SUMMARY OF THE INVENTION

A cotton dispenser according to the present invention includes a spool configured to receive a cotton strand thereabout and that rotates when the cotton strand is unwound therefrom. The dispenser includes a feed assembly downstream from the spool configured to receive an end of the cotton strand and unwind it from the spool when actuated. A cutting assembly is downstream from the feed assembly and configured to receive the cotton strand from the feed assembly. The cutting assembly includes a blade movable from a retracted configuration not in contact with the cotton strand and an activated configuration that severs the received cotton strand. The cotton dispenser includes a discharge chute in operative communication with the cutting assembly for guiding severed cotton portions to an outlet opening. A first input switch is electrically configured to actuate the feeding assembly so long as the input button is depressed and to actuate the cutting assembly when released.

Therefore, a general object of this invention is to provide a powered cotton dispenser that enables a user to dispense a selected size or number of cotton portions at the press of a button.

Another object of this invention is to provide a powered cotton dispenser, as aforesaid, that unwinds cotton from a pre-loaded spool so long as an input button is depressed and then automatically cuts the unwound portion when the input button is released.

Still another object of this invention is to provide a powered cotton dispenser, as aforesaid, that selectively delivers a user-selected quantity of cotton or a predetermined quantity of cotton.

Yet another object of this invention is to provide a powered cotton dispenser, as aforesaid, that indicates when the pre-loaded supply of cotton is running low.

A further object of this invention is to provide a powered cotton dispenser, as aforesaid, that enables a user to replace a pre-loaded cotton spool or to manually wind a new strand of cotton about an original spool.

A still further object of this invention is to provide a powered cotton dispenser, as aforesaid, that is easy to use and cost-effective to manufacture.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 4a is a front view of the cotton dispenser as in FIG. 1;

FIG. 4b is a sectional view taken along line 4b-4b of FIG. 4a;

DESCRIPTION OF THE PREFERRED EMBODIMENT

Figure 1:
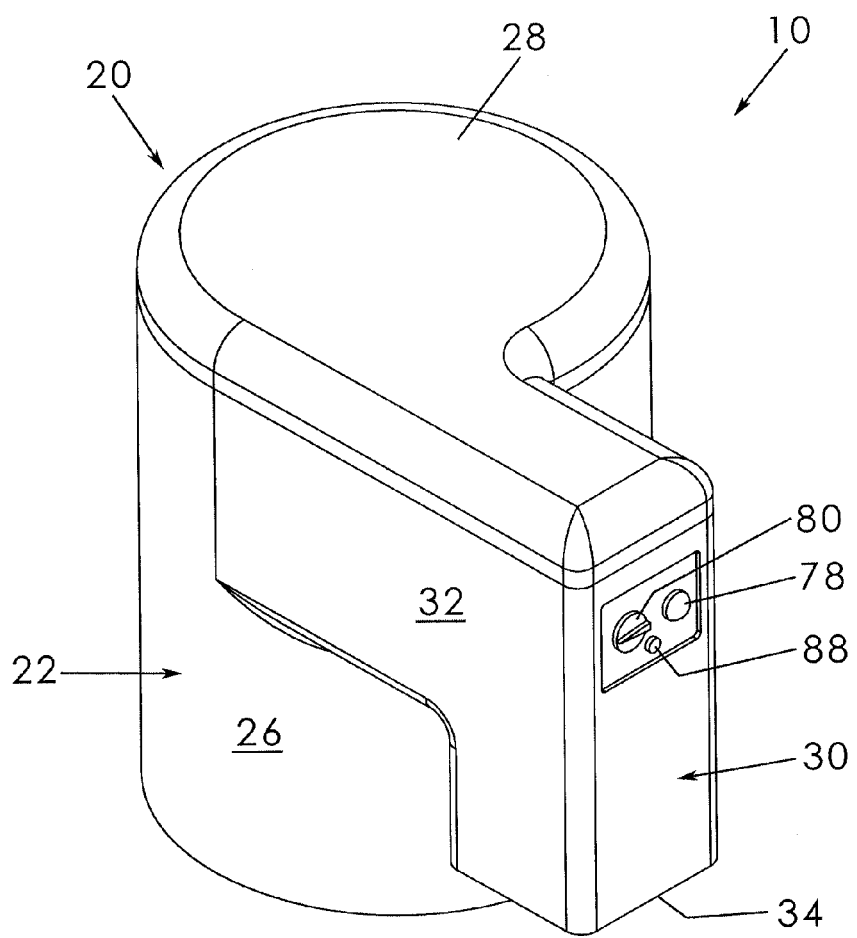
FIG. 1 is a perspective view of a cotton dispenser according to an embodiment of the present invention.

A cotton dispenser according to the present invention will now be described in detail with reference to FIGS. 1 to 6 of the accompanying drawings. The cotton dispenser 10 includes a spool 40, a feed assembly 50, and a cutting assembly 70. With the cotton dispenser 10, a strand of cotton (not shown) may be controllably removed from the spool 40, cut into a desired size, and dispensed as described below.

The cotton dispenser 10 includes a housing 20 having a main portion 22 and a discharge chute 30. The main portion 22 of the housing 20 includes a floor 24 with at least one side wall 26 extending upwardly therefrom such that the housing 20 defines an interior space. A removable access lid 28 is removably coupled to an upper edge of the side wall 26 such that the lid 28 prevents access to the interior space when in a closed configuration and enables access thereto when removed. It is understood that the lid 28 may be hingedly attached or coupled in a friction fit arrangement, snap fit arrangement, or the like. Access to the interior space enables replacement or replenishment of the spool 40 as will be described in greater detail later.

A base 42 having a circular configuration is rotatably mounted to the floor 24 of the main portion 22 of the housing 20. Specifically, the base 42 is axially mounted to the housing floor 24 and is free to revolve about its axis when urged to do so as will be described later. In addition, the base 42 may include a plurality of bearings or similar rollers 44 spaced apart about a circumferential edge that may be in contact with the housing side wall 26 so as to enhance the smoothness and efficiency of rotation of the base 42.

Figures 2A, 2B:
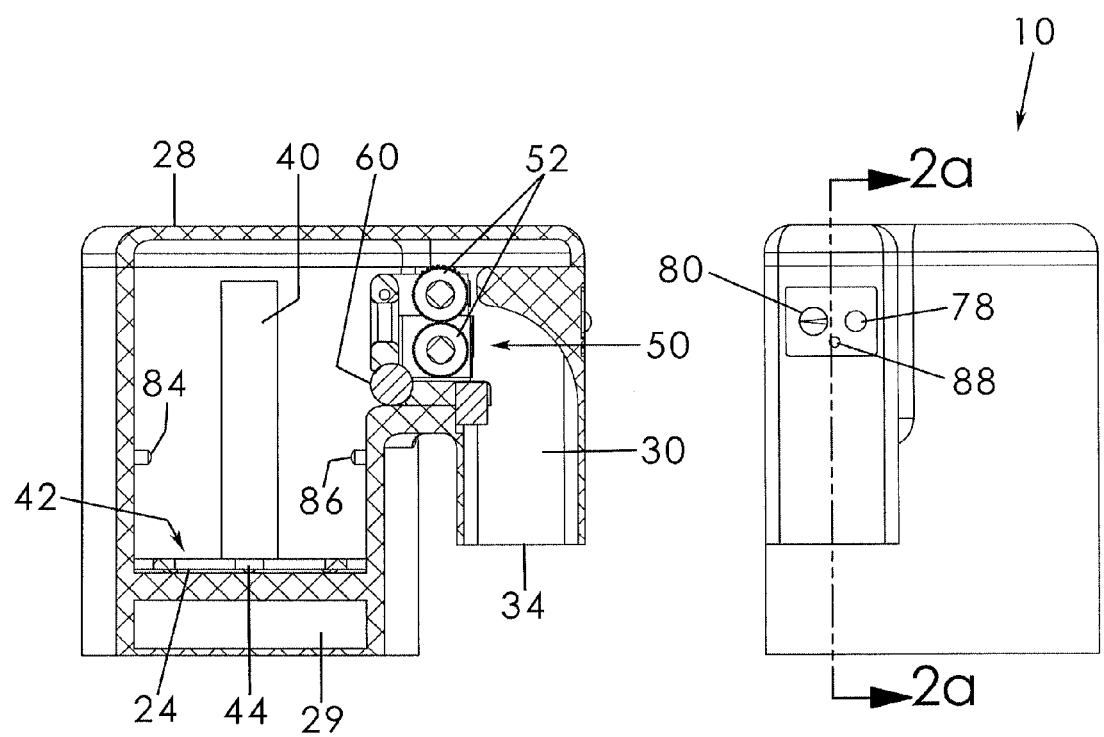
FIG. 2a is a sectional view taken along line 2a-2a of FIG. 2b.
FIG. 2b is a side view of the cotton dispenser as in FIG. 1.
Figure 3:
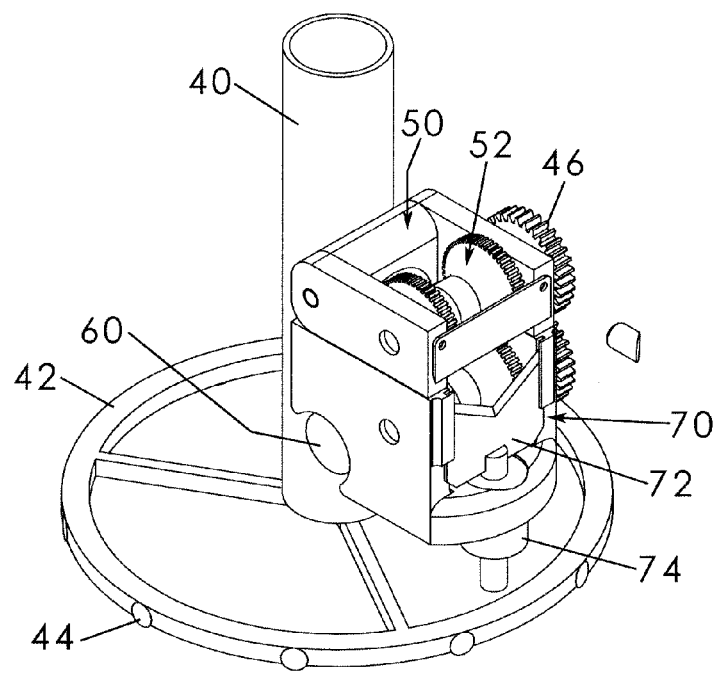
FIG. 3 is a perspective view of the cotton dispenser as in FIG. 1 with the housing removed.

The spool 40 preferably includes a generally cylindrical configuration and is vertically coupled to the base 42. The spool 40 is mounted in an upstanding or vertical configuration within the housing interior space (FIG. 2a). The cylindrical configuration of the spool 40 enables an elongate strand of cotton to be wound thereabout and then unwound by a user during operation of the cotton dispenser 10. The spool 40 and base 42 are rotated together as the cotton strand is unwound according to the description herein. It is understood that the spool 40 may be removably coupled to the base 42 such that the spool 40 may be selectively removed so that a user may wind a new strand of cotton thereabout or just replace the spool 40 with a pre-wound quantity of cotton.

Figure 5:
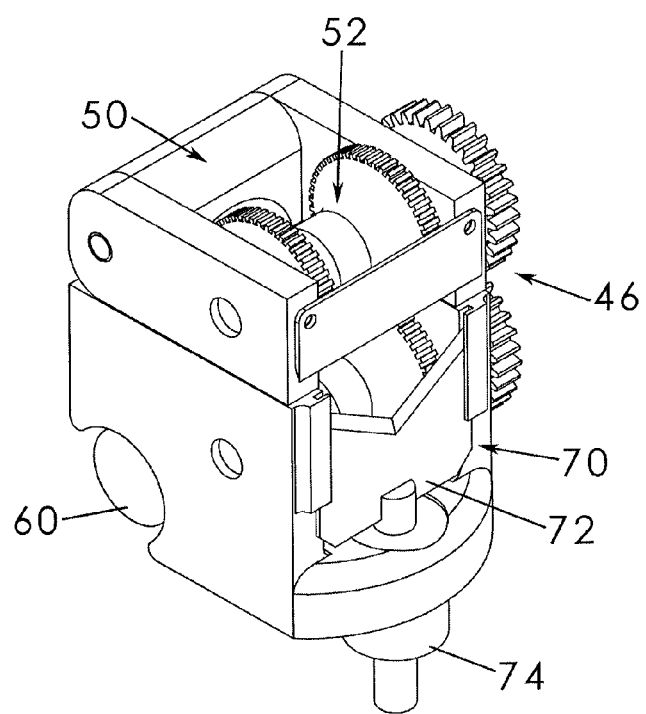
FIG. 5 is an isolated perspective view of the feeding and cutting assemblies as in FIG. 3.
Figure 6:
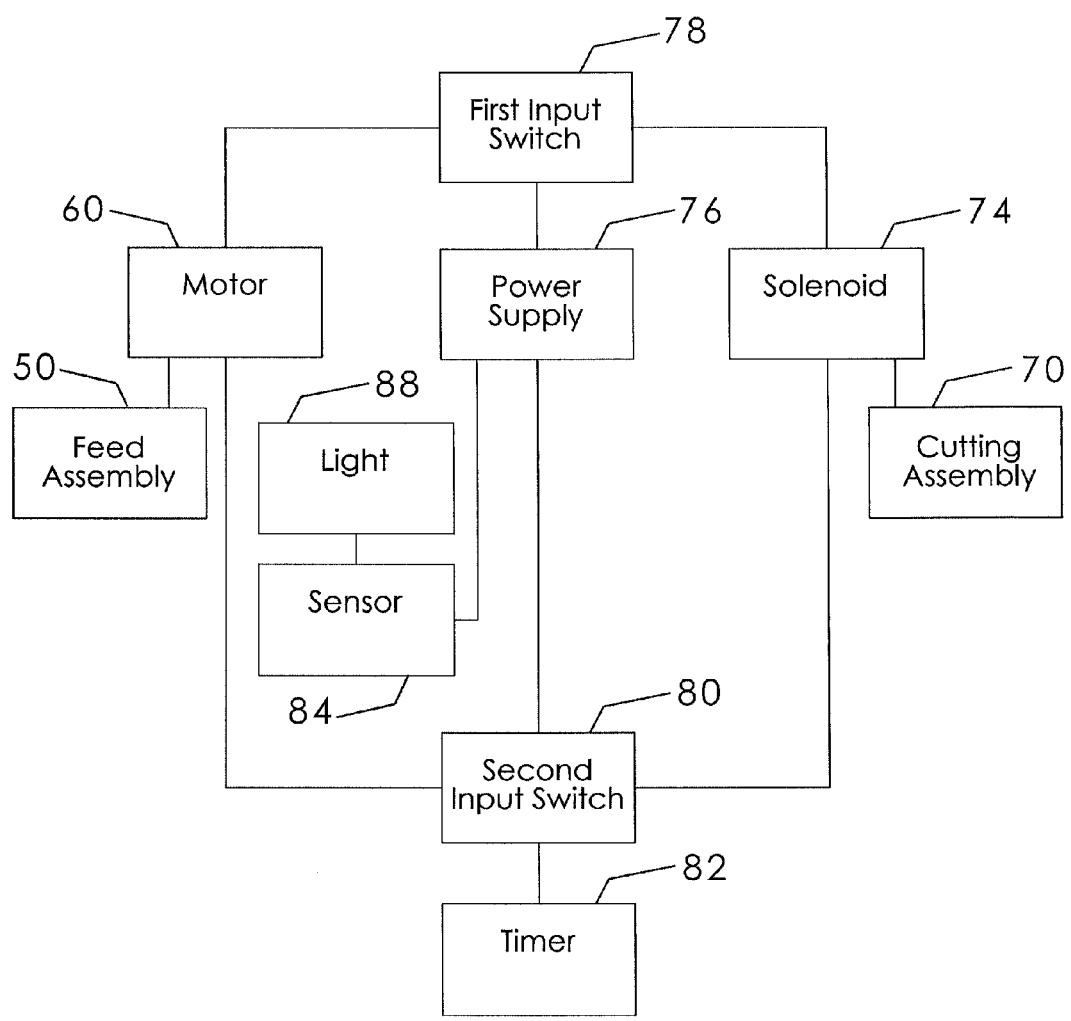
FIG. 6 is a block diagram illustrating the operative and electronic components of the present invention.

The feed assembly 50 is situated downstream of the spool 40 (FIGS. 2a, 3a, and 5). The feed assembly 50 preferably includes a rotary motion feed configuration although a linear feed configuration would also work. More particularly, the feed assembly includes a pair of counter-rotating rollers 52 that are powered by a motor 60 and which essentially pinch the strand of cotton therebetween. When the pair of rollers 52 is actuated to rotate, the strand of cotton is continuously pulled from the spool through the rollers 52. It is understood that an end of the cotton strand may have to be initially inserted into the rollers when a filled spool 40 is first inserted into the housing 20, but remains pinched between the pair of rollers 52 after that.

The cotton dispenser 10 includes a motor 60 situated in the interior space of the housing 20. The motor 60 is operatively and electrically connected to the feed assembly, such as with a gear train 46 (FIG. 5). When the motor 60 is energized, the pair of rollers 52 is actuated to rotate and rotation thereof pulls the cotton strand therethrough. In other words, actuation of the rollers unwinds the cotton strand from the spool 40, rotating the spool 40 as the cotton is unwound.

The cutting assembly 70 is situated downstream from the feed assembly 50. Preferably, the cutting assembly 70 is immediately adjacent or even integrally constructed with the feed assembly 50 (FIG. 5). Specifically, the cutting assembly 70 includes a blade 72 that is slidably movable between a retracted configuration not in contact with the cotton strand (FIG. 5) and an activated configuration at which the strand of cotton pulled through the pair of rollers 52 is severed. The cutting assembly 70 further includes means for actuating the blade to move from the normally retracted configuration to the activated configuration. Preferably, the means for actuating the blade 72 is a solenoid 74 operatively coupled to the blade 72 opposite the blade sharp edge such that the solenoid 74 pushes the blade to the activated condition quickly, automatically, and with high velocity when the solenoid 74 is energized.

The discharge portion 30 of the housing 20 includes side walls 32 connected to the side wall 26 of the main portion 22. The main portion 22 and discharge portion 30, in fact, may be a unitary or integral construction (FIG. 1). The walls of the discharge portion 30 define an opening, such as an open bottom 34 situated substantially in alignment with the downstream portion of the cutting assembly 70. In other words, as portions of the strand of cotton are severed, they fall through the discharge portion opening 34.

Preferably, the power source 76 is a battery although A/C power would also work. The housing 20 defines a battery compartment 29—preferably below the floor 24 of the main portion 22 as shown in FIG. 2a although other positions within the housing 20 would also work. The cotton dispenser 10 includes a first input switch 78 situated on the outside of the housing 20, such as on the side wall 32 (FIG. 1) so as to be conveniently accessible to a user. For embodiments having only a single input switch, the first input switch 78 may be referred simply as "an input switch." The first input switch 78 is electrically connected to the power source 76, motor 60, and solenoid 74. The first input switch 78 is configured, such as through wiring, circuitry, or processor programming to energize and to continue energizing the motor 60 when the switch is depressed and continues to be depressed. In other words, the motor 60 actuates the pair of rollers 44 to pull/unwind the strand of cotton from the spool 40 into the rollers 52 until the first input switch 78 is released. The first input switch 78 is also electrically connected to the solenoid 74 and configured, through wiring, circuitry, or programming to energize the solenoid 74 to activate when the first input switch 78 is released. It is well known in the art that when a solenoid is energized, its shaft is immediately and automatically extending outwardly or "popped out." In the present case, activation of the solenoid 74 causes the blade 72 to be slidably moved so as to sever the strand of cotton that is extended from the feed assembly 50 past the blade 72. When it is described above the first input switch 78 "energizes" the motor 60 or solenoid 74, it is understood that the first input switch 78 may simply permit power from the power source 76 to be directed to the motor 60 or solenoid 74, respectively, as indicated in the block diagram of FIG. 8.

In some embodiment, the cotton dispenser 10 may also include a second input switch 80 that is also electrically connected to the power source 76, motor 60, and solenoid 74. However, the second input switch 80 is configured to energize the motor 60 to operate for a predetermined amount of time. In other words, a predetermined amount of the cotton strand would be unwound and fed through the pair of rollers 52 before the solenoid 74 would be energized to activate the blade 72. The duration of motor activation may be regulated by a timer circuit 82 coupled to the second input switch 80. In this embodiment, all of the cotton portions discharged through the discharge portion/chute 30 would be identical in weight, volume, and configuration.

In some embodiments, a photosensor 84 may be mounted inside the interior space of the housing 20 generally adjacent the spool 40. The photosensor 84 may include a companion reflector 86 mounted opposite the main body of the photosensor 84 for reflecting a light back to the main body. In operation, the photosensor 84 may be positioned to detect when a predetermined level of the cotton strand has been removed. The photo sensor 84 may be electrically coupled to a warning light 88 and activates the light 88 when the photo sensor 84 detects the low cotton level. The photo sensor 84, of course, is electrically connected to the power source 76.

In use, a user may initially open the lid 28 and insert a spool 40 pre-wound with cotton or remove an empty spool 40 and manually wind it with cotton. Then the strand of cotton may be initially inserted between the pair of rollers 52 of the feed assembly. When a cotton ball is desired, the first input switch 78 may be depressed and held until a desired amount of cotton has been drawn from the spool 40. Upon releasing the button, the cutting assembly 70 is actuated to sever the cotton and it is automatically discharged. In some embodiments, the warning light 88 will be illuminated when the supply of cotton is too low.

It is understood that while certain forms of this invention have been illustrated and described, it is not limited thereto except insofar as such limitations are included in the following claims and allowable functional equivalents thereof.

The invention claimed is:

1. A cotton dispenser, comprising:
a housing having a main portion and a discharge chute downstream from said main portion, said housing having a floor, at least one side wall extending upwardly from said floor, and a lid removably coupled to an upper edge of said at least one side wall, said lid being movable between a closed configuration preventing access to said spool and an open configuration providing access to said spool; wherein said floor and said at least one side wall define an interior space, wherein said housing main portion and said discharge chute are in operative communication;
a spool having a generally cylindrical configuration so as to receive an elongate strand of cotton wound thereabout, said spool being configured to rotate axially when said strand of cotton is unwound therefrom;
a feed assembly situated downstream from said spool that is configured to receive said strand of cotton, said feed assembly causing said strand of cotton to unwind from said spool when actuated;
wherein said feed assembly includes a pair of counter-rotating rollers that sandwich said strand of cotton therebetween and pull said strand of cotton away from said spool when actuated;
a cutting assembly downstream from said feed assembly and configured to receive said strand of cotton after passing through said feed assembly, said cutting assembly having a blade movable between a retracted configuration not in contact with said strand of cotton and an activated configuration that severs said strand of cotton;
a power source;
a solenoid electrically connected to said power source and operatively connected to said blade to actuate said blade to move from said retracted configuration to said activated configuration when energized;
a motor electrically connected to said feed assembly;
a gear train operatively coupled to said motor and said pair of rollers, said gear train configured to rotate said pair of rollers when said motor is energized;
an input button electrically connected to said power source, said motor, said feed assembly, and said cutting assembly, said input button being configured to energize said motor to actuate said feed assembly when said input button is depressed and to energize said solenoid to move said blade when said input button is released; a base rotatably mounted to said floor of said housing, said spool being removably coupled to said base such that said spool and said base revolve relative to said housing floor when said strand of cotton is unwound from said spool and such that said spool is selectively removable from said base; wherein said base includes a plurality of spaced apart rollers positioned along a peripheral edge of said base and configured to bear against an interior surface of said at least one sidewall of said housing such that said base rotates with minimal friction when said feed assembly unwinds said cotton from said spool.

2. The cotton dispenser as in claim 1, further comprising a second input button electrically connected to a timer, said motor, said feed assembly, and said cutting assembly, said second input button configured to actuate said feed assembly until expiration of said timer prior to actuating said cutting assembly.

3. The cotton dispenser as in claim 1, further comprising:
a photosensor positioned in said housing interior space generally adjacent said spool so as to detect the presence or absence of said strand of cotton;
a light positioned on said housing and electrically connected to said photosensor; and
wherein said photosensor is electrically connected to said power source, said photosensor being configured to actuate said light if said photosensor detects that said strand of cotton includes less than a predetermined quantity.

4. A cotton dispenser for dispensing portions taken from an elongate strand of cotton, comprising:
a housing having a main portion and a discharge chute downstream from said main portion, said housing having a floor, at least one side wall extending upwardly from said floor, and a lid removably coupled to an upper edge of said at least one side wall, said lid being movable between a closed configuration preventing access to said spool and an open configuration providing access to said spool; wherein said floor and said at least one side wall define an interior space, wherein said housing main portion and said discharge chute are in operative communication;
a spool having a generally cylindrical configuration so as to receive said elongate strand of cotton wound thereabout, said spool being configured to rotate axially when said strand of cotton is unwound therefrom;
a feed assembly situated downstream from said spool that is configured to receive said strand of cotton, said feed assembly causing said strand of cotton to unwind from said spool when actuated;
wherein said feed assembly includes a pair of counter-rotating rollers that sandwich said strand of cotton therebetween and pull said strand of cotton away from said spool when actuated;
a cutting assembly downstream from said feed assembly and configured to receive said strand of cotton after passing through said feed assembly, said cutting assembly having a blade movable between a retracted configuration not in contact with said strand of cotton and an activated configuration that severs said strand of cotton;
a power source;
a solenoid electrically connected to said power source and operatively connected to said blade for moving said blade from said retracted configuration to said activated configuration when energized;
wherein said discharge chute defines a first end in communication with a downstream portion of said feed assembly and a second end displaced from said first end, said second end defining an open bottom through which cotton portions are dispensed after being severed from said strand of cotton;
a base rotatably mounted to said floor of said housing, said spool being removably coupled to said base such that said spool and said base revolve relative to said housing floor when said strand of cotton is unwound from said spool and such that said spool is selectively removable from said base; wherein said base includes a plurality of spaced apart rollers positioned along a peripheral edge of said base and configured to bear against an interior surface of said at least one sidewall of said housing such that said base rotates with minimal friction when said feed assembly unwinds said cotton from said spool; a motor electrically connected to said feed assembly and to said power source;
a first input button electrically connected to said power source, said motor, said feed assembly, and said cutting assembly, said first input button being configured to energize said motor to actuate said feed assembly when said first input button is depressed and to energize said means for activating said blade when said first input button is released.

5. The cotton dispenser as in claim 4, further comprising a second input button electrically connected to a timer, said power source, said motor, said feed assembly, and said cutting assembly, said second input button configured to actuate said feed assembly until expiration of said timer prior to actuating said cutting assembly.

6. The cotton dispenser as in claim 4, further comprising:
a photosensor positioned in said housing interior space generally adjacent said spool so as to detect the presence or absence of said strand of cotton;
a light positioned on said housing; and
wherein said photosensor and said light are electrically connected to said power source, said photosensor being configured to enable said light to be energized by said power source if said photosensor detects that said strand of cotton includes less than a predetermined quantity.

7. The cotton dispenser as in claim 4, wherein said power supply is a battery, said housing defining a battery compartment configured to receive said battery therein.

8. The cotton dispenser as in claim 4, further comprising a gear train operatively coupled to said motor and said pair of rollers, said gear train configured to rotate said pair of rollers when said motor is energized.

* * * * *